United States Patent
Obel

(10) Patent No.: US 6,745,074 B1
(45) Date of Patent: Jun. 1, 2004

(54) IMPLANTABLE HEART STIMULATOR WITH AUTOMATIC ADJUSTMENT OF THE SENSITIVITY SETTING

(75) Inventor: Martin Obel, Danderyd (SE)

(73) Assignee: St. Jude Medical AB, Järfälla (SE)

(*) Notice: Subject to any disclaimer, the term of this patent is extended or adjusted under 35 U.S.C. 154(b) by 0 days.

(21) Appl. No.: 10/009,668

(22) PCT Filed: May 11, 2000

(86) PCT No.: PCT/SE00/00937

§ 371 (c)(1),
(2), (4) Date: Nov. 13, 2001

(87) PCT Pub. No.: WO00/69518

PCT Pub. Date: Nov. 23, 2000

(30) Foreign Application Priority Data

May 12, 1999 (SE) ................................ 9901746

(51) Int. Cl.[7] .............................................. A61N 1/375
(52) U.S. Cl. .......................................................... 607/9
(58) Field of Search ................... 128/901, 902; 607/9; 600/509, 521, 508, 510, 517

(56) References Cited

U.S. PATENT DOCUMENTS 4,513,743 A    4/1985  van Arragon et al.
5,292,341 A  * 3/1994  Snell ............................ 607/30
6,539,259 B1 * 3/2003  Weinberg et al. ................ 607/9

FOREIGN PATENT DOCUMENTS

EP    0 321 764    6/1989

OTHER PUBLICATIONS

"Elektrokardiografisk mätteknik," Jacobsson, Medicin och Tecknik, 4th Edition (1995) p. 206.
"Elektriskt test," Lindgren et al., Pacemakern och hjärtat (1992) pp. 174–175.

* cited by examiner

Primary Examiner—Angela D. Sykes
Assistant Examiner—Roderick Bradford
(74) Attorney, Agent, or Firm—Schiff Hardin LLP

(57) ABSTRACT

An implantable heart stimulator has an electrode lead adapted to detect electrical heart signals and a cardiac activity sensor connected to the electrode lead for detecting heart signals above a sensitivity level. A heart signal classifier is also connected to the electrode lead, and classifies the incoming heart signals in a histogram with regard to their respective peak amplitude values. The heart signal classifier has a sensitivity level lower than the sensitivity level of the cardiac activity detector so that incoming heart signals are included in the histogram data which are below the level that would be detected by the cardiac activity detector. An analyzer in communication with the classifier and the activity detector analyzes the histogram data and adjusts the sensitivity level of the activity detector dependent on the histogram data.

11 Claims, 4 Drawing Sheets

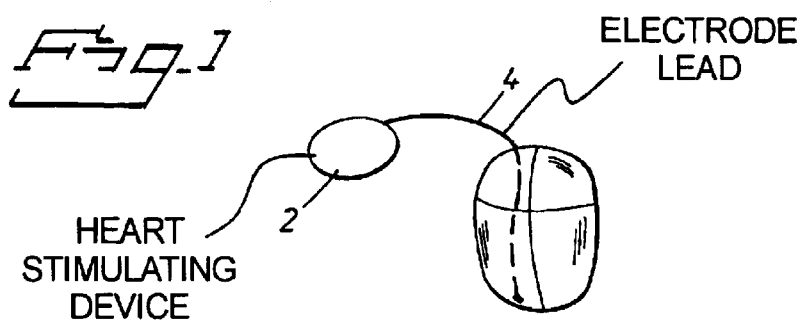
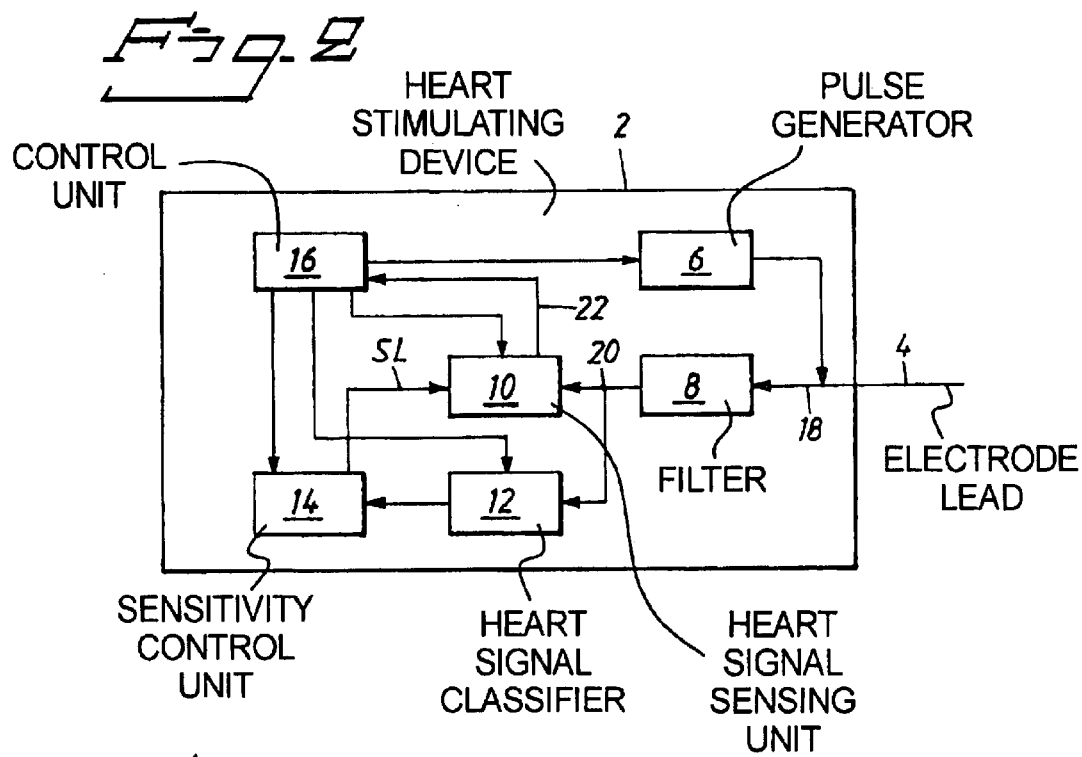
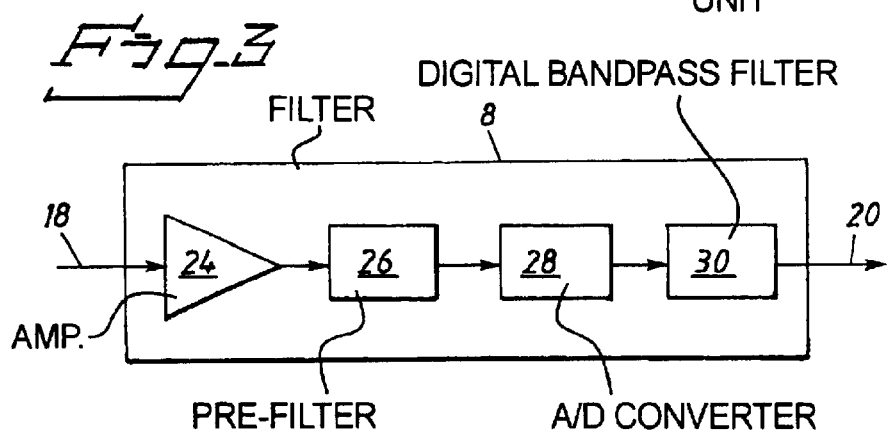

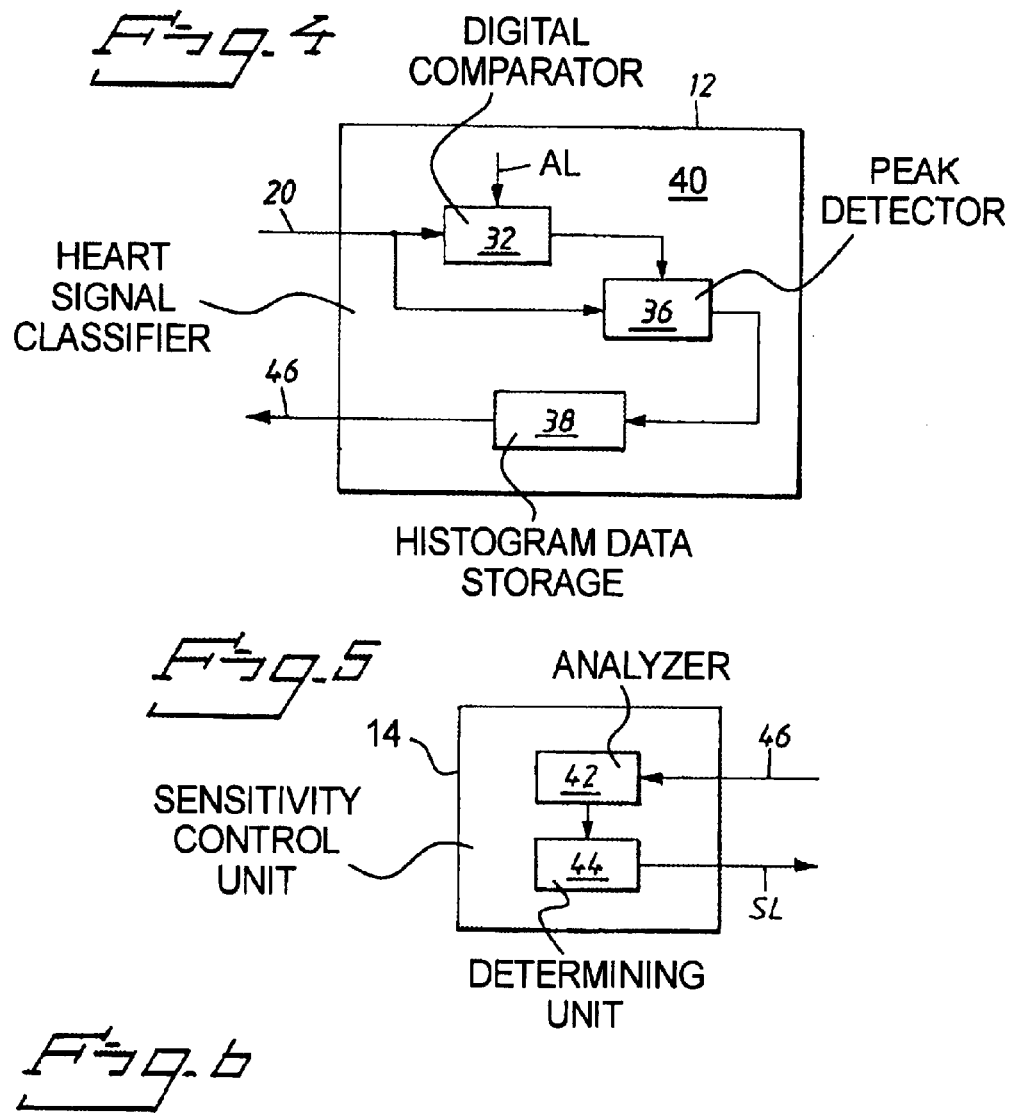
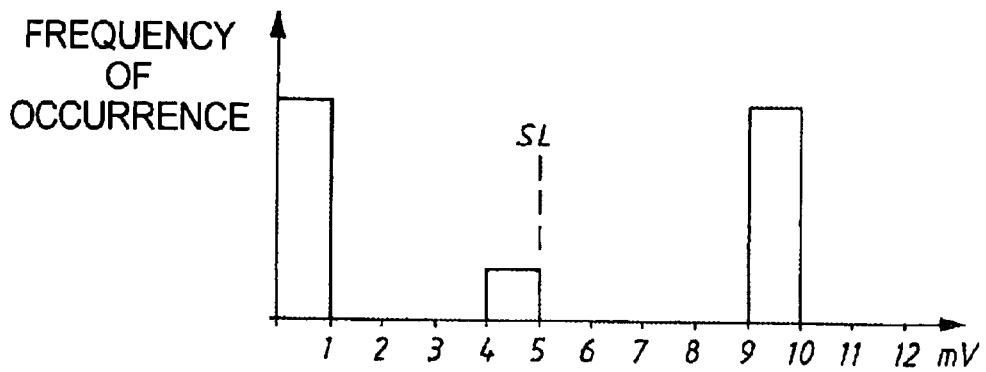

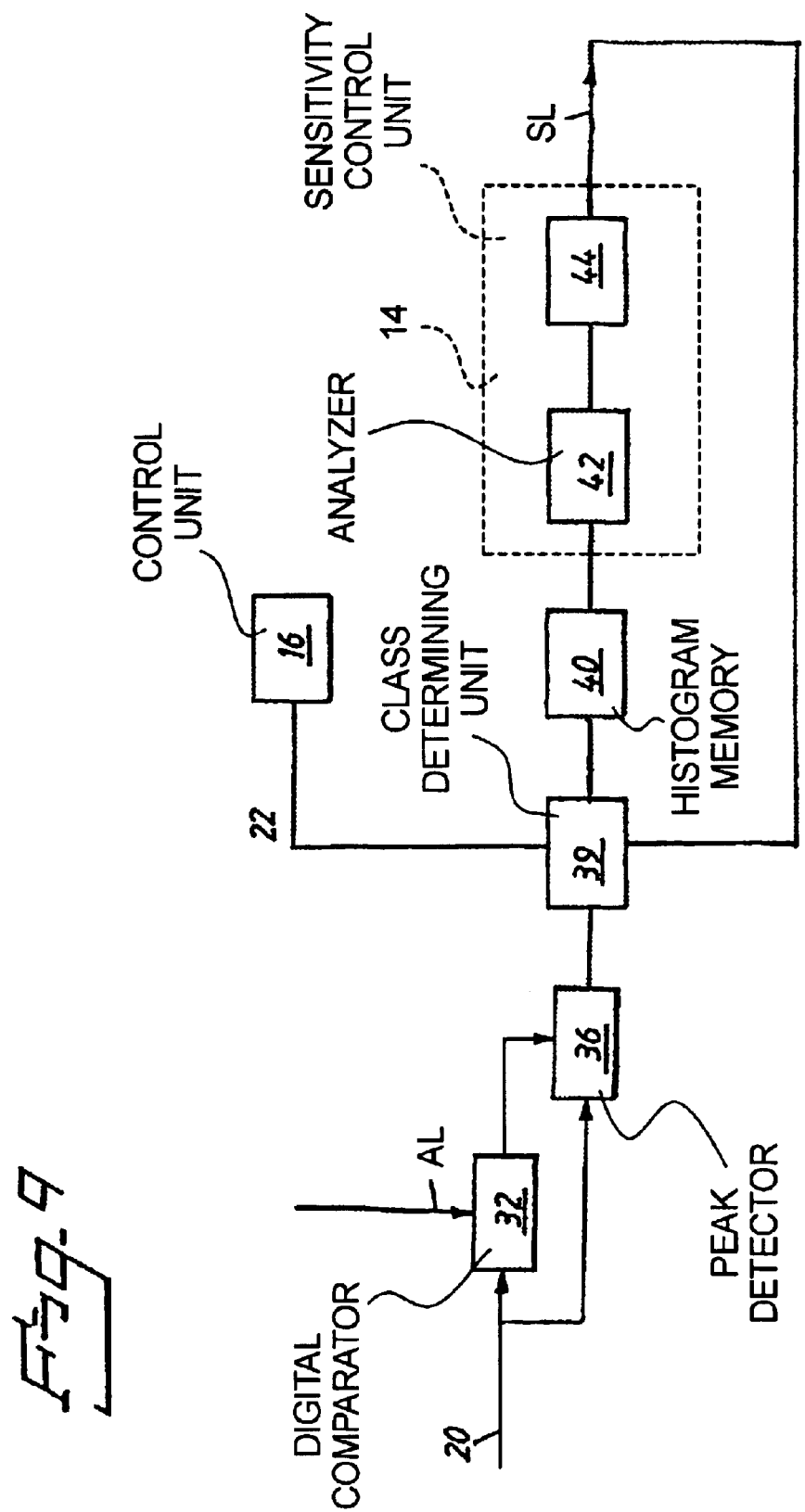

IMPLANTABLE HEART STIMULATOR WITH AUTOMATIC ADJUSTMENT OF THE SENSITIVITY SETTING

TECHNICAL FIELD OF THE INVENTION

The invention relates to an implantable heart stimulator set forth in the preamble of the independent claim.

BACKGROUND OF THE INVENTION

The sensitivity is a pacemaker parameter, which determines the lowest amplitude of a heart signal to which the device's sense amplifier will respond. Sensitivity is stated in millivolts. Note that the higher millivolt value, the lower the sensitivity. If, for example, the sensitivity is 6 mV, a signal has to be 6 mV or larger before the signal is recognized; on the other hand, if the sensitivity is 2 mV, a signal only has to be 2 mV or larger before it is recognized. Thus, the lower the mV value, the more sensitive the device.

A ventricular event occurring early in the heart cycle (prior a normally timed QRS-complex) and arising from a focus in the ventricles is often referred to as a premature ventricular contraction (PVC).

If a PVC not is detected due to undersensing it can result in that inappropriately timed, asynchronous or competitive stimulation pulses are delivered. Undersensing is defined as a failure of the pacemaker to sense an electrical signal related to a heart event, e.g. a PVC, due to that the sensitivity of the sensing circuit of the pacemaker is too low. This can often be corrected by programming the pacemaker to a more sensitive setting, i.e. decreasing the value of the sensitivity level.

U.S. Pat. No. 4,513,743 discloses a device, e.g. a cardiac pacemaker, adapted for implantation in a human patient. The implanted device comprises circuitry for registering the occurrence of sensed or evoked events and means for classifying registered events into respective classes of one or more parameters associated with the events. The device is arranged, on demand, to communicate these data to an external device that is arranged to present it in a histogram convenient for further analysis. The purpose of these analyses could be e.g. for making diagnosis, to have a more complete history of the device operation and the patient response thereto and to be able to make a judgement concerning the programming of the device. For a cardiac pacemaker sensed events include e.g. QRS-waves, P-waves and PVCs and examples of parameters include peak QRS-amplitude, peak P-amplitude and A-V interval.

U.S. Pat. No. 5,292,341 discloses a method and a system for determining and automatically adjusting the sensor parameters of a rate responsive pacemaker. A sensor indicated rate (SIR) histogram is established and processed by an external programmer. Instructions are given to a physician to collect diagnostic data from the pacemaker and the patient and the system then calculates a new set of operating parameters that, according to one embodiment, automatically is programmed into the pacemaker. The operating parameters or sensor control parameters are e.g. a threshold parameter, a reaction time parameter and a slope parameter. They all control, in different ways, how the raw sensor signal should be processed.

EP-A-0 321 764 discloses an event detector in which an optimal setting of the detector sensitivity is achieved by passing the input signal through a circuit which measures the signal's maximal values, then establishes the difference between the maximal values and the established threshold, and, in a preferred embodiment, controls the threshold in accordance with the difference and a given desired threshold value.

Many factors influence the characteristics, e.g. the amplitude and the morphology, of the heart signals. These factors could be the use of drugs and the activity and respiration of the patient. The sensitivity settings of the heart signal detectors in an implantable pacemaker is normally done based on the amplitude of the heart signal observed at the time when the programming of the pacemaker is performed at the implantation and at follow-ups. Many of the above-mentioned factors change over time which might result in an inappropriate setting of the sensitivity level of the heart signal detectors.

Another aspect is that it is a lengthy and complicated procedure during follow-up examinations to review and analyze all parameter settings of the pacemaker in order to make appropriate changes.

The main object of the invention is to take changes of amplitude values of the heart signal during a predetermined period of time into account for setting a sensitivity level of a heart signal sensing means of an implantable heart stimulator. In particular to be able to identify PVCs with a peak amplitude below the sensitivity level.

An additional object of the invention is to shorten the time of programming the heart stimulator at follow-up examinations.

SHORT DESCRIPTION OF THE INVENTIVE CONCEPT

These objects are achieved according to a heart stimulator having the characterizing features of the independent claim. Preferred embodiments are set forth in the dependent claims. According to an alternative embodiment is the analysis and determination performed in an extracorporeale programming device.

SHORT DESCRIPTION OF THE APPENDED DRAWINGS

FIG. 1 shows an implantable heart stimulator.

FIG. 2 shows an implantable heart stimulating device according to the invention.

FIG. 3 shows filter means.

FIG. 4 shows heart signal classifying means according to the invention.

FIG. 5 shows sensitivity control means according to the invention.

FIG. 6 shows a histogram illustrating the invention.

FIG. 9 shows an alternative embodiment of this invention in which the signal classifying means and signal sensing means are combined into a common means.

DETAILED DESCRIPTION OF PREFERRED EMBODIMENTS OF THE INVENTION

Figure 7:
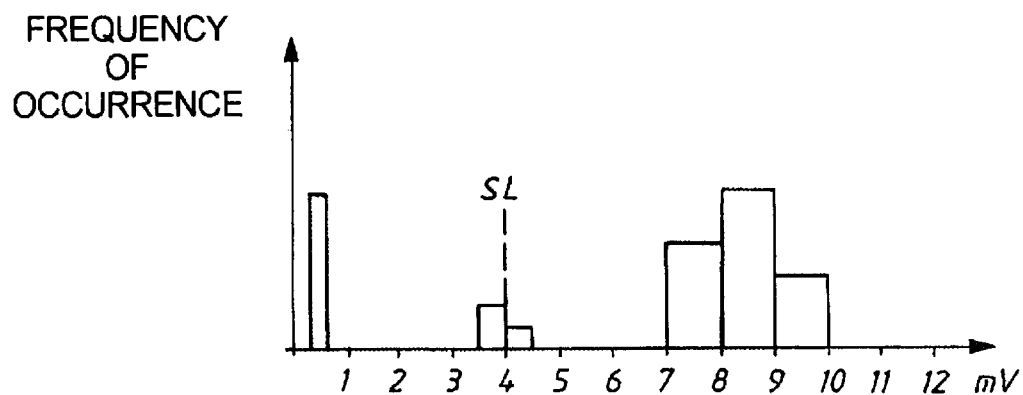
FIG. 7 shows a histogram illustrating a preferred embodiment of the invention.

The invention will now be described in greater detail with references to the appended drawings.

FIG. 1 discloses an implantable heart stimulator comprising a heart stimulating device 2 and one heart electrode lead 4. The electrode lead is inserted into the heart and arranged in the ventricle according to procedures well known to persons skilled in the art. The heart stimulator disclosed in FIG. 1 relates to a single chamber heart stimulator, which means that the electrode lead is arranged in one chamber of the heart, in this case the right ventricle. However, it should be noted, that the invention is equally applicable in a dual chamber heart stimulator that comprises two heart electrode leads adapted to stimulate the heart both in the atrium and in the ventricle and also in a multi-chamber heart stimulator adapted to stimulate three or four chambers of the heart.

FIG. 2 discloses the implantable heart stimulating device 2 according to the invention that comprises a pulse generator 6 for generating heart stimulating pulses to the heart via electrode lead 4. The heart stimulating device 2 further comprises a filter means 8 connected to the electrode lead 4, a heart signal sensing means 10 having a sensitivity level SL, a heart signal classifying means 12, a sensitivity control means 14 and control means 16. A heart signal 18 obtained by the electrode lead is applied to filter means 8 for amplification, AD-conversion and filtration. A filtered heart signal 20 is applied to the heart signal sensing means 10 and to the heart signal classifying means 12. If the amplitude of the filtered heart signal 20 exceeds the sensitivity level SL then the heart signal sensing means 10 will generate a detection signal 22 to the control means 16.

The peak values of the filtered heart signal 20 are stored as histogram data by the heart signal classifying means 12 as will be described in further details below. The histogram data is accessible by the sensitivity control means 14. The control means 16 controls the function of heart stimulator, e.g. the implementation of different stimulating modes. For sake of simplicity all the means comprised by the heart stimulating device 2 are not disclosed in FIG. 2, such means could be sensor means and power supply means.

As obvious to persons skilled in the art some of the above-described means can be implemented in a microprocessor.

Before further describing the present invention some general remarks and definitions with regard to the use of the term histogram are made. A histogram is a graphical representation of data and is constructed of data collected in a frequency table. A frequency table is constructed by dividing scores into intervals and counting the number of scores in each interval. In the present invention it is the histogram data (frequency table) that is analyzed and the histograms shown in the figures are only for illustration of the invention.

FIG. 3 discloses the filter means 8 that comprises amplifying means 24, prefiltering means 26, e.g. a low pass anti-aliasing filter, an A/D converter 28 and a digital band-pass filter 30 with a pass band of 20–50 Hz. The filtered heart signal 20 is a stream of bits.

FIG. 4 discloses the heart signal classifying means 12 that comprises a digital comparing means 32 with an adjustable level AL preferably set to a value that avoids detection of noise, e.g. in the interval of 0,1–1,5 mV, a peak detector 36 and a histogram data storage 38.

If the detection is made between two poles inside the heart using a bipolar electrode less noise is detected compared to if detection is made between one pole inside the heart and the heart stimulating device.

The bit-stream of the filtered heart signal 20 is applied both to the digital comparing means 32 and to the peak detector 36. The comparing means 32 generates a peak detection signal 40 to the peak detector 36, if, during a predetermined detection window, e.g. 20 ms., the amplitude value exceed the adjustable level AL provided that more than e.g. 20 ms have elapsed since the last detection. When the peak detector receives a peak detection signal 40 it stores the peak amplitude value in the histogram data storage 38 in the class representing that peak amplitude value.

During said detection window of a predetermined length, e.g. between 10 and 20 ms., the peak amplitude value is determined. This can be done by measuring the maximal peak to peak difference, by measuring the peak amplitude over a baseline or by measuring the intrinsic deflection peak amplitude.

Alternatively the peak detector may store the maximal peak amplitude that has occurred from the point in time when the amplitude exceeded the adjustable level AL until the point in time when it has a value lower than AL.

In the above description the signal sensing means and the signal classifying means have been illustrated as being separate entities. The functions of these means may however be combined more or less completely into a common means for instance by incorporating the sensitivity level SL into the signal classifying means. Thus, if the classifying means determines that the cardiac signal has a peak amplitude>SL then an inhibiting signal would be generated by the heart signal classifying means and sent to the control means 16. An example is disclosed in FIG. 9. The digital comparator 32 is set at adjustable level AL. The peak detector 36 provides a peak value as described in under FIG. 4. The class determining means (39) that determines to which class the actual signal belongs also generates a synchronization signal 22 to the control means 16 if the peak amplitude exceeds the set sensitivity SL. The histogram memory 45 is updated for each cardiac signal with a peak amplitude exceeding AL. Analyzing means 42 and sensitivity determining means 44 forming the sensitivity control means 14 serves for determination of the new level SL if necessary.

The described measurement technique is well known to a person skilled in the art of pacemakers and is therefore not further described in this application.

The above mentioned measurement technique is only given as an example since the invention is applicable in a heart stimulator using other measurement techniques resulting in amplitude values that can be used as histogram data in accordance with present invention.

FIG. 5 discloses the details of the sensitivity control means 14 that comprises an analyzing means 42 and a determining means 44. The analyzing means 42 receives at predetermined time intervals, e.g. every hour, once a day or once a week, data 46 representing the histogram from the histogram data storage 38. Based upon the analysis of the histogram data a new sensitivity level SL is determined that is applied to the heart signal sensitivity means 10. The analysis and how the new sensitivity level is determined will be described in greater detail below.

The detected peak amplitude values are stored in the histogram data storage 38 as histogram data with classes, preferably equally wide, representing the peak amplitude of the heart signal on the x-axis and the number of occurrences in each class on the y-axis. The width of each class can be chosen to any value between 0,1 and 4 mV, preferably in the range 0,5–2 mV. If the width is chosen in the region close to 0,1 mV the histogram is similar to a continuous curve and it is then possible to approximate the histogram with an appropriate curve.

A histogram that illustrates the present invention is disclosed in FIG. 6. The width of each class is 1 mV. Theoretically the number of T-waves should equal the number of R-waves, but since the amplitude of the T-wave is small it is possible that not all T-waves are detected. The sensitivity level SL is set to 5 mV. In this case a number of heart signals representing premature ventricular contractions (PVCs) with amplitudes of 4–5 mV have been identified. Since this amplitude values are below the sensitivity level the PVCs are not detected by the heart signal sensing means which in turn can lead to improper timing of the heart stimulator.

In accordance with the present invention the histogram data is analyzed and based on that analysis the sensitivity level is lowered to e.g. 3.5 mV and the PVCs are thus detected and proper timing of the heart stimulator is established.

When analyzing the histogram data some assumptions are to be made. T-waves, PVCs and R-waves can be distinguished from each other because they typically have different peak amplitudes. It is therefore assumed that a detected heart signal with peak amplitude in the range of e.g. 6–12 mV emanates from an R-wave and that a detected heart signal with peak amplitude in the range of e.g. 4–6 mV emanates from a PVC. The amplitude of a T-wave is, as indicated above, small, in the interval of 1% to 3% of the R-wave amplitude, e.g. not greater than 0,3 mV if the R-wave amplitude is 10 mV, and then also much smaller than the amplitude of a PVC.

The values defining these ranges are of course dependent on how the amplitude values are measured. The ranges exemplified above are applicable if the peak amplitude is measured in the way described above in relation with FIG. 4.

When the heart stimulator is delivered from the manufacturer the sensitivity level SL is typically set to 4,0 mV, this is called the "shipped setting" of the stimulator. During the first weeks following the implantation of the heart stimulator many factors influence the detected peak amplitude, e.g. the degree of in-growth of the stimulation electrode tip in the heart wall influence the current density. It is therefore often necessary to set the sensitivity level to a new value at follow-up visits at the hospital. As a rule of thumb, based on experience, the sensitivity level is set to 50% of the R-wave peak amplitude.

The analysis performed by the analyzing means 42 can be made in many different ways. One important object with the invention is to identify PVCs with a peak amplitude below the sensitivity level SL. It is therefore checked if any detected heart signals with peak amplitude in the range of the interval assigned for PVCs, e.g. 4–6 mV, fall in that range.

The number of occurrences in the class (or classes) within the PVC range must preferably exceed a predetermined number to be taken into account for further analysis. This predetermined number is dependent on the predetermined time interval, e.g. every hour, once a day or once a week, that the analyzing means 42 receives data from the histogram storage 38. This may for instance be initiated from the control means 16.

If is established that a predetermined number of PVCs have occurred a value representing the detected PVCs, e.g. the lowest amplitude value or a mean value, is compared to SL, e.g. by taking the difference between these values or by forming the quote.

If it is determined that the value representing PVC is less than SL, or close to SL, the determining means 44 will determine a new sensitivity level SL.

One way is to set SL to a value, e.g. 1 mV, lower than the value representing PVC provided that the new SL exceeds a lowest allowable value chosen to be well above typical T-wave amplitude values.

Another way is to identify the classes falling within the ranges defining the R-waves, e.g. 6–12 mV, determine a value representing those classes and as a first step set a provisional SL to 50% of this value representing the R-waves. Then compare this provisional SL to the value representing PVC and set SL to the provisional SL if the provisional SL is less than the value representing PVC. These two ways of determining the sensitivity level SL can of course also be combined.

As a general rule is the sensitivity level determined and set to a value so that all amplitudes with an amplitude greater than a typical T-wave amplitude are detected.

FIG. 7 discloses a histogram with different width of the classes; e.g. in the range 0,25–2 mV is the width 0,25 mV, in the range 2–6 mV is the width 0,5 mV and above 6 mV is the width 1 mV.

The classes falling in the ranges representing R-wave amplitudes and the T-wave amplitudes, respectively, are identified and classes in-betweens are considered to relate to PVCs. In this case the sensitivity level SL is lowered to 3,5 mV to secure detection of all PVCs.

A large variability of the amplitude values of the R-waves, i.e. many classes within the R-wave range, is an indication that the sensitivity level might be changed. The reason for varying R-wave amplitudes might be the influence of noise, e.g. interference with electrical signals from muscles or external disturbances.

The study of the variability can also be used for discrimination of T-wave amplitudes from noise. The former has quite a distinct peak at e.g. 0,2 mV while the latter are more spread out in the range of e.g. 0,1 and 1,5 mV.

Still another way to determine SL is to use some kind of pattern recognition to identify the different parts of the histogram and then to relate them to SL.

Once a new sensitivity level SL is determined it is applied to the heart signal sensing means 10.

Figure 8:
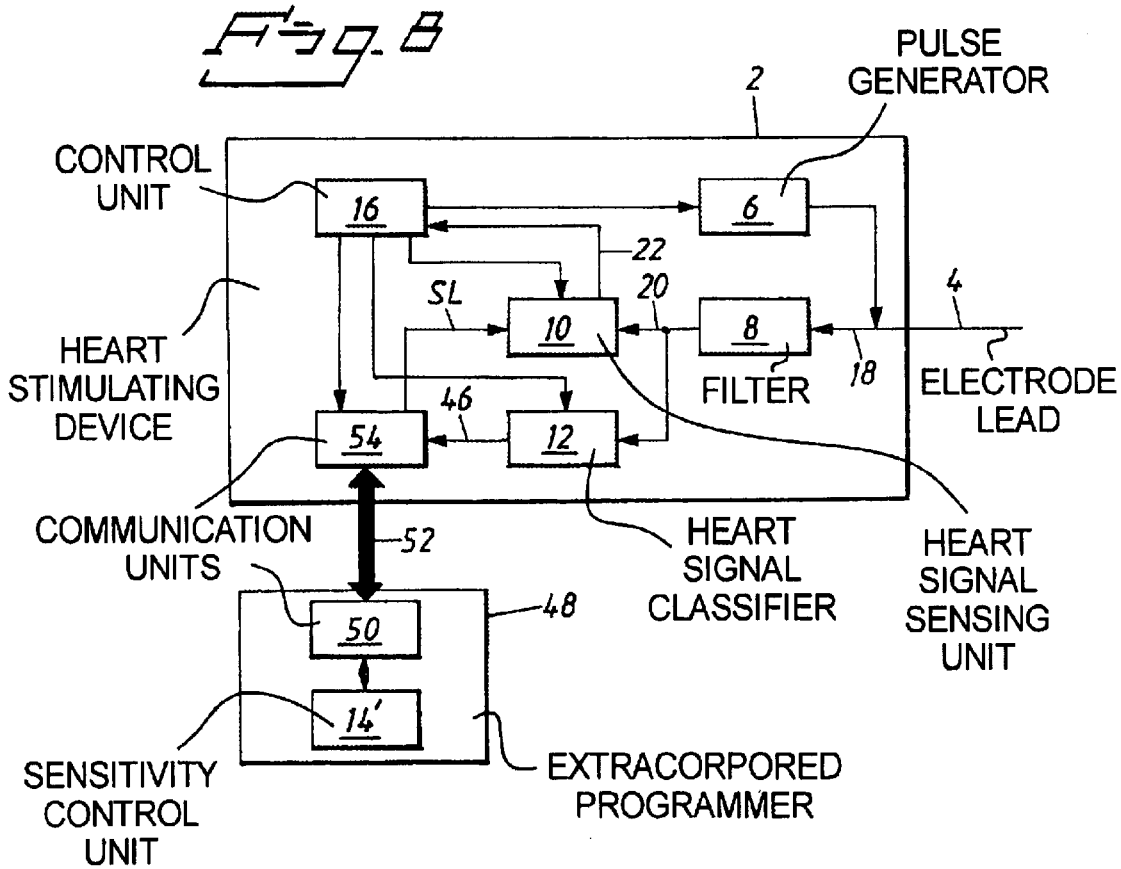
FIG. 8 shows an alternative embodiment of the invention.

FIG. 8 discloses an alternative embodiment of the present invention where the implantable heart stimulator is modified in that the sensitivity control means is arranged in an extracorporeale (i.e. outside the patient's body) programming device 48. The programming device 48 comprises communication control means 50 that controls the transfer of data 52 to and from the heart stimulating device and sensitivity control means 14'. The heart stimulating device 2 as disclosed in FIG. 2 is modified in that a communication unit 54 is arranged adapted to receive and send data, e.g. data 46 representing the histogram from the histogram data storage 38, to the programming device 48. All other means disclosed in FIG. 8 have the same function and the same reference signs as in FIG. 2 and for further description of the embodiment disclosed in FIG. 8 it is therefore referred to the description of the embodiment disclosed in FIG. 2.

The transfer of data between the stimulating device 2 and the programming device 48 is preferably made by radio waves.

The communication technique used in the present invention is not further described because it is not considered necessary for understanding of the invention. Furthermore, a person skilled in the art is aware of several different communication protocols that could be used for transfer data between a programming device and an implanted heart stimulator.

The present invention is not limited to the above-described preferred embodiments. Various alternatives, modifications and equivalents may be used. Therefore, the above embodiments should not be taken as limiting the scope of the invention, which is defined by the appending claims.

I claim:

1. An implantable heart stimulator comprising:
   a cardiac activity detector, supplied with incoming electrical heart signals each having a peak amplitude value, said incoming electrical heart signals including signals representing a premature ventricular contraction, if said premature ventricular contraction has occurred, said cardiac activity detector having a first sensitivity level and detecting heart signals, among said incoming electrical heart signals, having a peak amplitude value exceeding said first sensitivity level;
   a heart signal classifier, also supplied with said incoming electrical heart signals, for classifying the respective peak amplitude values of said incoming electrical heart signals as histogram data according to the respective peak amplitude values, said heart signal classifier having a second sensitivity level, which is lower than said first sensitivity level, allowing updating of said histogram data with peak amplitudes of heart signals among said incoming electrical heart signals having a peak amplitude that is below said first sensitivity level; and
   an analyzer in communication with said classifier and supplied with said histogram data from said classifier, and in communication with said cardiac activity detector for setting said first sensitivity level thereof to include detection of said signals representing a premature ventricular contraction, dependent on an analysis in said analyzer of said histogram data.

2. An implantable heart stimulator as claimed in claim 1 wherein said analyzer analyzes said histogram data and resets said first sensitivity level at predetermined time intervals.

3. An implantable heart stimulator as claimed in claim 1 wherein said heart signal classifier classifies said histogram data in a plurality of classes of said peak amplitude values, and wherein said analyzer analyzes said histogram data by determining whether said incoming electrical heart signals are respectively in classes falling within a predetermined range of peak amplitude values.

4. An implantable heart stimulator as claimed in claim 3 wherein said predetermined range includes peak amplitude values representing premature ventricular contractions.

5. An implantable heart stimulator as claimed in claim 4 wherein, if said analyzer determines that said classes fall within said predetermined range of peak amplitude values, said analyzer determines an amplitude value representing said classes and compares said amplitude value to the first sensitivity level currently set in said cardiac activity detector.

6. An implantable heart stimulator as claimed in claim 5 wherein, if said analyzer determines that said amplitude value is below said first sensitivity level, said analyzer sets a new first sensitivity level at a value lower than said amplitude value.

7. An implantable heart stimulator as claimed in claim 3 wherein said predetermined range includes peak amplitude values representing R-waves.

8. An implantable heart stimulator as claimed in claim 7 wherein, if said analyzer determines that said classes fall within said predetermined range, said analyzer determines an amplitude value representing said classes.

9. An implantable heart stimulator as claimed in claim 8 wherein said analyzer sets a new first sensitivity level at a value in a range between 40% and 60% of said amplitude value.

10. An implantable heart stimulator as claimed in claim 9 wherein said analyzer sets said new first sensitivity level at a value that is 50% of said amplitude value.

11. An implantable heart stimulator as claimed in claim 1 further comprising an extracorporeal programming device interacting by telemetry with said heart signal classifier and said cardiac activity detector, and wherein said analyzer is disposed in said extracorporeal programming device.

* * * * *